US010159593B2

(12) United States Patent
Evans

(10) Patent No.: US 10,159,593 B2
(45) Date of Patent: Dec. 25, 2018

(54) ORTHOPEDIC CAST AND SPLINT BANDAGES WITH ENCAPSULATED HARDENING MEDIUM AND METHOD

(71) Applicant: BSN medical, Inc., Charlotte, NC (US)

(72) Inventor: John C. Evans, NR Rochdale (GB)

(73) Assignee: BSN MEDICAL, INC., Charlotte, NC (US)

( * ) Notice: Subject to any disclaimer, the term of this patent is extended or adjusted under 35 U.S.C. 154(b) by 1252 days.

(21) Appl. No.: 14/285,815

(22) Filed: May 23, 2014

(65) Prior Publication Data

US 2015/0005684 A1 Jan. 1, 2015

Related U.S. Application Data

(60) Provisional application No. 61/840,841, filed on Jun. 28, 2013.

(51) Int. Cl.
| | | |
|---|---|---|
| *A61F 13/04* | (2006.01) | |
| *A61F 5/058* | (2006.01) | |
| *A61L 15/08* | (2006.01) | |
| *A61L 15/12* | (2006.01) | |

(52) U.S. Cl.
CPC ............. *A61F 5/058* (2013.01); *A61F 13/04* (2013.01); *A61L 15/08* (2013.01); *A61L 15/12* (2013.01)

(58) Field of Classification Search
CPC .. A61L 15/07; C08L 75/04; A61F 5/01; A61F 5/058; Y10T 428/249955; Y10T 428/249978; Y10T 442/171; Y10T 442/174; Y10T 442/198
USPC ........... 602/5, 6, 8; 206/389, 440; 428/321.5
See application file for complete search history.

(56) References Cited

U.S. PATENT DOCUMENTS

| | | | |
|---|---|---|---|
| 4,482,414 A | 11/1984 | Schonberger | |
| 4,770,299 A | 9/1988 | Parker | |
| 4,869,046 A | 9/1989 | Parker | |
| 4,996,979 A | 3/1991 | Grim et al. | |

(Continued)

FOREIGN PATENT DOCUMENTS

| | | |
|---|---|---|
| WO | WO 01/19420 A1 | 3/2001 |
| WO | WO 2005/102228 A1 | 11/2005 |
| WO | WO 20061081164 A2 | 8/2006 |

OTHER PUBLICATIONS

International Search Report for PCT/US2014/039292 dated Aug. 1, 2014.

*Primary Examiner* — Ophelia A Hawthorne
*Assistant Examiner* — Caitlin Carreiro
(74) *Attorney, Agent, or Firm* — Shumaker, Loop & Kendrick, LLP

(57) ABSTRACT

A medical bandaging product that includes a flexible medical material including an elongate fabric, a reactive system, and microspheres. In certain aspects, a component of the reactive system is homogeneously impregnated into or coated throughout the flexible medical material without being encapsulated in the microspheres such that the reactive system remains stable and non-activated in the absence of an activating agent, and hardens upon activation by exposure to the activating agent to form a rigid, self-supporting structure. In this aspect, the microspheres are homogeneously impregnated into or coated throughout the flexible medical material, the microspheres encapsulate an activating agent and are configured to release the activating agent to form the rigid, self-supporting structure.

15 Claims, 11 Drawing Sheets

(56) References Cited

U.S. PATENT DOCUMENTS

| | | |
|---|---|---|
| 5,003,970 A | 4/1991 | Parker et al. |
| 5,454,780 A | 10/1995 | Duback et al. |
| 5,861,149 A * | 1/1999 | Ritter .................. A61L 15/44 424/78.06 |
| 6,695,801 B1 | 2/2004 | Toronto et al. |
| 6,719,710 B2 * | 4/2004 | Darcey ................ A61F 13/04 602/5 |
| 2006/0219350 A1 * | 10/2006 | Bain .................... B29C 65/76 156/247 |
| 2011/0300767 A1 * | 12/2011 | Gedanken ............ D06P 5/2011 442/123 |

* cited by examiner

ORTHOPEDIC CAST AND SPLINT BANDAGES WITH ENCAPSULATED HARDENING MEDIUM AND METHOD

CROSS-REFERENCE TO RELATED APPLICATION

This application claims priority from U.S. Application No. 61/840,841 filed Jun. 28, 2013, the entirety of which is incorporated herein by reference.

TECHNICAL FIELD AND BACKGROUND OF THE INVENTION

The present invention generally relates to medical bandage products. In particular, the present invention relates to an orthopedic splinting product and a casting product, both utilizing a substrate that can be used to stabilize a fracture or sprain or any other injury that requires a rigid or semi-rigid support and that includes a unique manner of transforming the products from a soft, conformable state to a rigid state suitable for immobilizing a wounded limb. A method of manufacturing and using the bandages is also disclosed.

Medical bandages for use in the treatment of injuries, such as broken bones requiring immobilization of a body member, are generally formed from a strip of fabric or scrim material impregnated with a substance which hardens into a rigid structure after the strip has been wrapped around the body member.

Conventional practice has been to fabricate a cast or splint upon an injured limb by initially applying to the limb a protective covering of a cotton fabric or the like, and then overwrapping the covering and limb with a substrate impregnated with plaster-of-paris or a substrate formed from flexible fiberglass fabric layers impregnated with a moisture-curable resin. Casts or splints formed from these materials possess several disadvantages. In particular, casts or splints formed using plaster-of-paris impregnated substrates have a relatively low strength to weight ratio. This results in a finished cast or splint having low strength that is very heavy and bulky. Furthermore, plaster-of-paris casts or splints are slow to harden, requiring 24 to 72 hours to reach maximum strength. Because plaster-of-paris breaks down in water, bathing and showering are difficult. Even if wetting due to these causes can be avoided, perspiration over an extended period of time can break down the plaster-of-paris and create a significant problem with odor and itching.

In order to alleviate the above-discussed disadvantages of the conventional cast or splint utilizing plaster-of-paris impregnated substrates, moisture-curable resin impregnated fiberglass substrates and resin-impregnated non-glass substrates formed from a knitted or woven fabric have been devised. The knitted fabric substrate provides a cast or splint that exhibits particularly good conformability, possesses sufficient rigidity when cured, and shows relatively little or no loss of strength.

Current synthetic splinting and casting products utilize moisture-curable resins to harden the cast tape or splint upon application. Because the chemistry is designed to harden upon exposure to moisture, these products are required to be packaged in low moisture conditions and maintained in a moisture-proof condition until just prior to application. The hardening reaction is typically initiated by wetting the product with water and then promptly applying and conforming the product to the limb as required before the cast or splint hardens.

This water hardenable resin is usually activated by either spraying water on the resin or cast or splint or dunking the device in water and squeezing the water into the bandage. In all these practices it is essential to saturate the casting tape or splint with water to ensure proper activation of the resin and hardening of the cast or splint.

These products have been very successful, but require specialized packaging in low moisture conditions and in relatively expensive multilayer plastic and metal foil packages. Even then, these products can become hard over a period of time or lead to deactivation of the chemical components (e.g., catalyst) as a result of trace amounts of moisture in the packaging, or because of moisture intrusion during removal of portions of the bandage material from roll-form type packaging. Cast tape and splint roll products manufactured and sold by BSN medical, Inc. under the trademark Orthoglass® comprise such products. Therefore, there is a need for a simpler, less-expensive yet easy to use moisture curable bandage, such as cast tape and splints.

BRIEF SUMMARY OF THE INVENTION

Therefore, it is an object of the invention to provide initially flexible casting and splinting products. These flexible bandages may include microspheres that contain water that when ruptured initiates hardening of the bandage.

It is another object of the invention to provide initially flexible bandages, such as casting and splinting products that include microspheres that contain a catalyst that when ruptured initiates hardening of the bandage.

It is an object of the invention to provide a medical bandaging product, that includes a flexible medical material including an elongate fabric, a reactive system, and microspheres. In certain aspects, a component of the reactive system is homogeneously impregnated into or coated throughout the flexible medical material without being encapsulated in the microspheres such that the reactive system remains stable and non-activated in the absence of an activating agent, and hardens upon activation by exposure to the activating agent to form a rigid, self-supporting structure. In this aspect, the microspheres are homogeneously impregnated into or coated throughout the flexible medical material, the microspheres encapsulate an activating agent and are configured to release the activating agent to form the rigid, self-supporting structure.

In certain aspects, the elongate fabric of the medical bandaging product includes a knitted material formed from monofilament or multifilament yarns including at least one of fiberglass, polyester, polyolefin, aramid, and polyamide.

In certain aspects, each filament of the monofilament or multifilament yarn has a diameter from 0.3 mm to 2 mm.

In certain aspects, the elongate fabric is surrounded by a non-woven material, an open cell foam, or a reticulated foam.

In certain aspects, the reactive system includes a polyurethane moisture curing system.

In certain aspects, the component of the reactive system that is homogeneously impregnated into or coated throughout the flexible medical material without being encapsulated in the microspheres includes a prepolymer, a polyol, or a combination thereof.

In certain aspects, the component of the reactive system that is homogeneously impregnated into or coated throughout the flexible medical material without being encapsulated in the microspheres includes a prepolymer, the prepolymer is at least one organic isocyanate selected from the group consisting of methylene diphenyl diisocyanate, toluene diisocyanate, hexamethylene diisocyanate, and isophorone diisocyanate.

In certain aspects, the microspheres include micelles or polymeric microspheres having a diameter of from 200 μm to 2000 μm that encapsulate water, a catalyst, or a combination thereof.

In certain aspects, the microspheres further encapsulate a prepolymer, the prepolymer is at least one organic isocyanate selected from methylene diphenyl diisocyanate, toluene diisocyanate, hexamethylene diisocyanate, and isophorone diisocyanate.

In certain aspects, the microspheres are polymeric microspheres made from a polyoxyethylene, polypropylene oxide, polylactic acid, polyethylene, polystyrene, poly(methyl methacrylate), polyvinyl pyrrolidone, polycaprolactone, or any combination thereof.

In certain aspects, the microspheres are homogeneous meaning that each microsphere encapsulates substantially the same chemical components/materials.

In certain aspects, the microspheres are heterogeneous meaning that two or more separate types of microspheres (i.e., microsphere mixtures) are present. The heterogeneous microspheres may include microspheres made from different chemical components (i.e., different polymers) and/or the heterogeneous microspheres may encapsulate different chemical components/materials when compared to one another.

In certain aspects, the disclosed medical bandage further includes an antimicrobial agent coated on the flexible medical material from 1 $g/m^2$ to 10 $g/m^2$.

In certain aspects, the flexible bandages are provided in packaging. The packaging may preferably be resealable. In certain aspects, the packaging may be moisture proof to potentially ensure longer shelf life of the bandaging product. However, in other aspects, the bandaging product may be packaged in inexpensive packaging that is not moisture proof. It is another object of the invention to provide initially flexible casting and splinting products that are light weight and conformable.

BRIEF DESCRIPTION OF THE DRAWINGS

Some of the objects of the invention have been set forth above. Other objects and advantages of the invention will appear as the invention proceeds when taken in conjunction with the following drawings, in which.

DETAILED DESCRIPTION OF THE INVENTION

Figure 1:
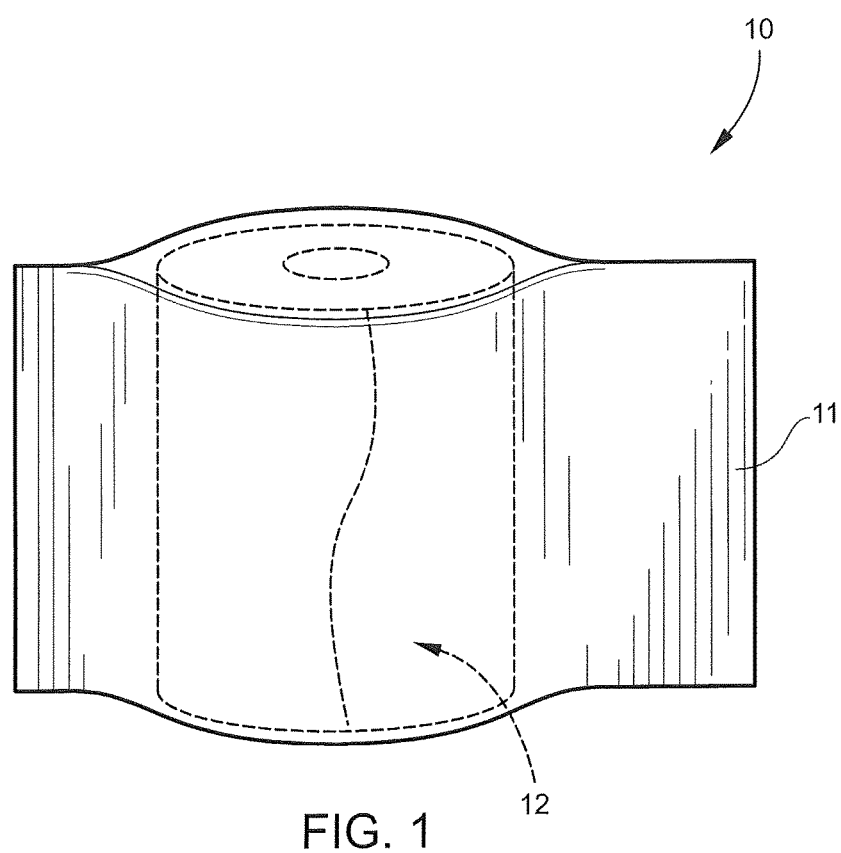
FIG. 1 shows a perspective view of a cast product including a storage package and a medical cast bandage.

Disclosed is a medical bandaging product, that includes a flexible medical material including an elongate fabric, a reactive system, and microspheres. In certain aspects, a component of the reactive system is homogeneously impregnated into or coated throughout the flexible medical material without being encapsulated in the microspheres such that the reactive system remains stable and non-activated in the absence of an activating agent, and hardens upon activation by exposure to the activating agent to form a rigid, self-supporting structure. In this aspect, the microspheres are homogeneously impregnated into or coated throughout the flexible medical material, the microspheres encapsulate an activating agent and are configured to release the activating agent to form the rigid, self-supporting structure.

Flexible Medical Material

The flexible medical material may include an elongate fabric constructed of a woven material (e.g., knitted material), non-woven material, or a combination thereof. For example, in certain aspects, the flexible medical material is a knitted elongate fabric. In certain aspects, the flexible medical material is a non-woven material. In certain aspects, the flexible medical material is an elongate fabric that includes a woven material forming the core of the flexible medical material and further including a non-woven material that surrounds the woven material.

The flexible medical material may be formed from fibers that include, but are not limited to, cotton, glass, fiberglass, polyester, polyolefin, aramid, para-aramid, polyamides, or any combination thereof. Examples of polyolefins include, but are not limited to, polyethylene, polypropylene, polybutene-1, or any combination thereof. For example, in certain aspects, the polyolefins may include linear low density polyethylene (LLDPE), low density polyethylene (LDPE), polyethylene (PE), linear high density polyethylene (LHDPE), or any combination thereof. In certain aspects, the polyester includes, but is not limited to, polyethylene terephthalate, polyglycolic acid, polylactic acid, polybutylene terephthalate, polytrimethylene terephthalate, or any combination thereof. Examples of polyamides include, but are not limited to, nylon (e.g., nylon-6,6, nylon-6, nylon-6,9, nylon-6,10, nylon-11, and nylon-4,6) In certain aspects, the fibers that form the flexible medical material are hydrophobic, and in a further aspect, these fibers may include a hydrophobic coating including, but not limited to, silicone based water-repellant coating or a fluorochemical (e.g., polytetrafluoroethylene) at a concentration ranging from 1 to 100 $g/m^2$, 1 to 50 $g/m^2$, 1 to 10 $g/m^2$, 1 to 5 $g/m^2$, 1 to 4 $g/m^2$, 1 to 3 $g/m^2$, 5 to 80 $g/m^2$, 7 to 50 $g/m^2$, 7 to 30 $g/m^2$, 8 to 20 $g/m^2$, 8 to 10 $g/m^2$.

In certain aspects, the fibers that form the flexible medical material may include monofilament or multifilament yarns having various diameters. These yarns may include textured, filamented, or fibrillated yarn. In certain aspects, each filament of the monofilament or multifilament yarns is from 0.03 mm to 2 mm, 0.04 mm to 1.5 mm, 0.05 mm to 1.0 mm, or any diameter range occurring within these endpoints.

In certain aspects, the flexible medical material is a knitted elongate fabric having between 100 and 1000 windows/cm$^2$, 100 and 750 windows/cm$^2$, 100 and 500 windows/cm$^2$, 100 and 250 windows/cm$^2$, 100 and 150 windows/cm$^2$, 100 and 125 windows/cm$^2$, 200 and 750 windows/cm$^2$, 200 and 500 windows/cm$^2$, 200 and 300 windows/cm$^2$, 200 and 250 windows/cm$^2$, 250 and 500 windows/cm$^2$, 250 and 300 windows/cm$^2$, 300 and 400 windows/cm$^2$, 400 and 500 windows/cm$^2$. In certain aspects, the flexible medical material is formed of a single layer of an elongate knitted double fabric configured to be impregnated (preferably homogeneously impregnated) with the reactive system and microspheres discussed below. In one preferred embodiment the splint or casting tape comprises a warp knitted double fabric impregnated with a moisture curable polyurethane resin (e.g., a component of the reactive system and the microspheres). In certain aspects, the warp knitted double fabric can be constructed using any of the materials listed above. The yarn count ranges are preferably between 20 Tex to 136 Tex, 25 Tex to 136 Tex, 30 Tex to 136 Tex, 40 Tex to 136 Tex, 44 Tex to 136 Tex, 50 Tex to 120 Tex, 60 Tex to 110 Tex, 70 Tex to 100 Tex, 80 Tex to 90 Tex.

In certain embodiments, the knitted elongate fabric of the flexible medical material is knitted on a double bed warp knitted machine with six guide bars. The preferred fabric notation is an inlay with a chain stitch on the surface and a "V," butterfly or atlas stitch in the center. The yarns are knitted into a substrate having sufficient weight and thickness to keep the resin within the substrate (e.g., knitted elongate fabric). For example, the thickness may include 0.5 mm to 10 mm, 0.5 mm to 7.5 mm, 0.5 mm to 5 mm, 0.5 mm to 2.5 mm, 1 mm to 10 mm, 1 mm to 8 mm, 1 mm to 6 mm, 1 mm to 4 mm, 1 mm to 2 mm, 2.5 mm to 7.5 mm, 2.5 mm to 5 mm, 3 mm to 6 mm, 3 mm to 4 mm, 4 mm to 5 mm.

In certain aspects, the knitted elongate fabric of the flexible medical material comprises 450-580 courses per meter, with a preferred range of 500-550 courses per meter and 50-90 wales per 10 centimeters, with a preferred range of 65-75 wales per 10 centimeters, and a most preferred value of 70 wales per 10 centimeters. Preferred knitted fabric widths of the flexible medical material range between 2.5 to 60 centimeters, 2.5 to 30 centimeters, 2.5 to 20 centimeters, 2.5 to 10 centimeters, 2.5 to 7.5 centimeters. The fabric thickness is an important feature as it affects the final rigidity and is also important aesthetically for patient's comfort and ease of use. The final fabric weight will depend on various factors such as fabric construction, yarns used and other factors. In the most preferred structure the fabric weight will vary in the range of 500 to 3000 g/m$^2$ and even more preferably in the range of 1000 to 1800 g/m$^2$.

In certain aspects, the flexible medical material includes a non-woven material that surrounds the knitted elongate fabric described above. In certain aspects, the non-woven material is formed from a polyolefin including, but not limited to, polypropylene or polyethylene. In certain aspects, the knitted elongate fabric may also be surrounded by open cell or reticulated foam, closed cell foam, soft flexible films (e.g., thermoplastic films).

In certain aspects, the flexible medical material further includes an antimicrobial agent. The antimicrobial agent can be either homogenously incorporated into, for example, the yarns used to form the knitted elongate fabric or the antimicrobial agent can be coated onto portions of the flexible medical material. For example, the antimicrobial agent may be coated on the woven materials, non-woven materials, or any combination thereof. In certain aspects, the flexible medical material includes 1 to 10 g/m$^2$, 1 to 8 g/m$^2$, 1 to 5 g/m$^2$, 1 to 4 g/m$^2$, or 1 to 3 g/m$^2$ of the antimicrobial agent. The antimicrobial agent may include copper, copper salts, silver, silver salts, nickel, nickel salts, or any combination thereof.

Reactive System

The medical bandaging product includes a reactive system that sufficiently hardens and aids in forming a desired cast or splint. In certain aspects, the reactive system chemically reacts to partially or completely harden the flexible medical material within 10 minutes to 3 hours, 10 minutes to 1 hour, 20 minutes to 2 hours, 20 minutes to 30 minutes after the activation of the reactive system, preferably during the application of the medical bandaging product to a user.

In certain aspects, the reactive system includes moisture curing systems having prepolymers, various chemical components with reactive groups, and a reaction initiator (e.g., an activating agent). These reactive groups may be capable of cross-linking and/or polymerizing reactions to form the desired polymer that hardens the flexible medical material when forming a splint or cast. For example, these reactive groups may include, but are not limited to, reactive amine groups, reactive hydroxyl groups, reactive thiol groups, reactive carboxylic acid groups, a reactive aldehyde group, a reactive ether group, a reactive ester group, or any combination thereof.

In certain aspects, the reactive system includes prepolymers, various chemical components having reactive groups, and initiators capable of forming polyurethanes via moisture curing reactions.

Examples of prepolymers may include, but are not limited to, isocyanates, and more specifically, these prepolymers may include organic polyisocyanates. Organic polyisocyanates include aliphatic and/or cycloaliphatic diisocyanates. Examples of organic isocyanates may include, but are not limited to, methylene diphenyl diisocyanate, toluene diisocyanate, hexamethylene diisocyanate, and isophorone diisocyanate. Detailed examples include aliphatic diisocyanates such as ethylene, 1,4-tetramethylene, 1,6-hexamethylene and 1,12-dodecane diisocyanates and cycloaliphatic diisocyanates such as cyclohexane-1,3 and -1,4 diisocyanates as well as any desired mixture of these isomers, 1-isocyanato-3,3,5-trimethyl-5-isocyanatomethylcyclohexane (IPDI), 2,4- and 2,6-hexahydrotoluene diisocyanate as well as any desired mixtures of these isomers, 4,4'- and 2,4'-diisocyanatodicyclohexylmethane. In certain aspects, only one organic polyisocyanate is included in the reactive system. In other aspects, mixtures ranging from 2 to 10, 2 to 6, 2 to 4, 3 to 5, or 4 to 8 organic polyisocyanates may be included in the reactive system to ensure that the medical bandage achieves sufficient hardness.

As previously discussed, the reactive system further includes various chemical components with reactive groups. Examples of these chemical components and reactive groups may include, for example, polyols. Polyols may include aliphatic polyols, aromatic polyols, or a combination thereof, and include on average two or more hydroxyl groups per molecule (R'—(OH)$_{n\geq 2}$) that may react with various prepolymers to form, for example, polyurethanes. In certain aspects, these polyols may include diols. These polyols may include polyester polyols prepared, for example, from dicarboxylic acids, preferably aliphatic dicarboxylic acids having 2 to 12, preferably 4 to 8 carbon atoms in the alkylene radical and multifunctional alcohols, preferably diols. Examples include aromatic dicarboxylic acids such as phthalic and terephthalic acids and aliphatic dicarboxylic acids such as glutaric acid, pimelic acid, suberic acid, azelaic acid, sebacic acid, undecanedioic acid, dodecanedioic acid, and, preferably, succinic acid and adipic acid. Examples of multifunctional, particularly bi- and tri-functional, alcohols are: ethylene glycol, diethylene glycol, 1,2-propylene glycol, trimethylene glycol, 1,3 propanediol, dipropylene glycol, 1,10-decanediol, glycerin, trimethylolpropane and, preferably, 1,4-butanediol and 1,6-hexanediol. In certain aspects, only one type of polyol is included in the reactive system. In other aspects, polyol mixtures ranging from 2 to 10, 2 to 6, 2 to 4, 3 to 5, or 4 to 8 different types of polyols may be included in the reactive system.

In certain aspects, these polyols may include a number average molecular weight ranging from 100 to 3000, 200 to 2,000, 250 to 1,000, 300 to 500, 400 to 700, 500 to 650. If the number average molecular weight exceeds 3,000, polymerization or cross-linking of the reactive system may occur too quickly. If the number average molecular weight falls below 100 to 200, polymerization or cross-linking of the reactive system may occur too slowly and result in very poor mechanical properties of the resulting cast or splint. In certain aspects, the polyols have hydroxyl numbers of from 2 to 500, 3 to 300, 4 to 100, 5 to 65.

These reactive systems further preferably include one or more initiators (e.g., a catalyst) capable of initiating a reaction among the individual components of the reactive system. These initiators may include, for example, water, organic dicarboxylic acids such as succinic acid, adipic acid, phthalic acid and terephthalic acid and, preferably, multifunctional, particularly di- and/or tri-functional alcohols such as ethylene glycol, 1,2-propylene glycol, 1,3-propanediol, diethylene glycol, dipropylene glycol, 1,4-butanediol, 1,6-hexanediol, glycerin, trimethylolpropane and pentaerythritol.

If desired, higher boiling solvents and additives may also be incorporated in the disclosed reactive systems. These include, for example, fillers, plasticizers, pigments, carbon black, molecular screens, agents to render the systems thixotropic, antioxidants, and other similar materials. The advantageous properties of the systems are not impaired by the addition of these substances. Also, in certain aspects, anti-foaming agents may be incorporated into the medical bandage to reduce foaming of the reactive system and to potentially reduce contact of the reactive system to a user's skin.

In certain aspects, one or more components of the reactive system are homogenously dispersed onto and/or within the flexible medical material. For example, in certain aspects, one or more components are homogeneously applied to and dispersed on the flexible medical material via a coating process. This coating process may include, but is not limited to, a chemical vapor deposition process, a physical vapor deposition process, a spray coating, dip coating, or any combination thereof. In certain aspects, the fibers and/or yarns of the flexible medical material may be manufactured to include one or more components of the reactive system within these fibers and/or yarns.

Microspheres

To potentially ensure longer shelf-life of the flexible medical material before use, it is preferred to separate one or more components of the reactive system to prevent and/or reduce a premature reaction and hardening of the bandage. By separating one or more components of the reactive system, the reactive system remains latent. To ensure longer shelf-life, one or more components of the reactive system can be included within microspheres. These microspheres preferably encapsulate and store the one or more components of the reactive system until application of the medical material to a user and/or until one desires to activate the reactive system to harden the flexible medical material thus forming the desired cast or splint.

In certain aspects, the microspheres may be manufactured from natural materials, synthetic materials, or a combination thereof. For example, the microspheres may include micelles (e.g., lipid containing micelles), polymeric microspheres, glass microspheres, ceramic microspheres, metal microspheres, or any combination thereof. The microspheres may preferably include polymeric microspheres or micelles, which are highly susceptible to mechanical shear. The micelles may include amphiphilic molecules having a polar, water-soluble part and a nonpolar, water-insoluble part. Examples of amphiphilic substances include but are not limited to surfactants, detergents, lipids, certain proteins, certain polysaccharides, certain modified proteins or polysaccharides, or any combination thereof. The polymeric microspheres may be a polymer made from one monomer. In the alternative, the microspheres may include copolymers, including but not limited to, alternating copolymers, periodic copolymers, block copolymers (e.g., diblock copolymers, triblock copolymers, etc.), graft copolymers, or any combination thereof. The polymeric microspheres may include, for example, polyethylene oxides (e.g., polyethylene glycol), polyoxyethylene (e.g., PEG-200, PEG-600, PEG-1000, PEG-2000), polypropylene oxide, poly lactic acid (e.g., poly(L-lactide)), polyethylene, polystyrene, poly (methyl methacrylate) (PMMA), polyvinyl pyrrolidone (PVP), polycaprolactone, or any combination thereof.

The disclosed microspheres have a diameter of from 2 µm to 2,000 µm, 50 µm to 2,000 µm, 200 µm to 2000 µm, 75 µm to 1,750 µm, 100 µm to 1,500 µm, 100 µm to 1,200 µm, 100 µm to 1,000 µm, 250 µm to 2,000 µm, 250 µm to 1,600 µm, 250 µm to 1,300 µm, 250 µm to 1,000 µm, 400 µm to 2,000 µm, 400 µm to 1,500 µm, 400 µm to 1,000 µm, 400 µm to 750 µm, 600 µm to 1,800 µm, 600 µm to 1,300 µm, 600 µm to 950 µm, 600 µm to 750 µm, 750 µm to 1,600 µm, 750 µm to 1,400 µm, 750 µm to 1,200 µm, 750 µm to 900 µm, 900 µm to 1,800 µm, 900 µm to 1,500 µm, 900 µm to 1,300 µm, 900 µm to 1,100 µm, 1,000 µm to 1,750 µm, 1,000 µm to 1,450 µm, 1,000 µm to 1,250 µm, or 1,000 µm to 1,100 µm.

In certain aspects, the microspheres include at least one component of the reactive system. For example, the microspheres may encapsulate at least one of the reaction initiators (e.g., catalyst and/or water), prepolymer, at least one chemical component with a reactive group, or any combination thereof. In preferred embodiments, the microspheres encapsulate a catalyst and/or water. In certain aspects, the microspheres may be homogeneous meaning that all microspheres encapsulate the same chemical components and all the microspheres are substantially identical. In other aspects, the microspheres may be heterogeneous mixtures meaning that certain microspheres differ from other microspheres. For example, in this heterogeneous microsphere mixture, it is envisioned that one type of microsphere may encapsulate, for example, the reaction initiator while another type of microsphere may encapsulate, for example, a prepolymer. In this heterogeneous microsphere mixture, the microspheres may be made from different components (e.g., different polymers, glass, etc.)

As previously discussed above, in certain preferred aspects, the reactive system is a moisture curing polyurethane system. In this aspect, the microspheres may preferably encapsulate at least water. In a further aspect, the microspheres may encapsulate water and one additional component selected from the prepolymer, polyol, and catalyst. It is further envisioned that homogeneous or heterogeneous microspheres may be used with the moisture curing polyurethane systems described herein.

In certain aspects, these microspheres are homogenously dispersed onto and/or within the flexible medical material. For example, in certain aspects, one or more components are homogeneously applied to and dispersed on the flexible medical material via a coating process. This coating process may include, but is not limited to, a chemical vapor deposition process, a physical vapor deposition process, a spray coating, dip coating, or any combination thereof. In certain aspects, the fibers and/or yarns of the flexible medical material may be manufactured to include the microspheres within these fibers and/or yarns.

It is preferable to select microspheres that are susceptible to shearing forces via manual manipulation (e.g., wringing the bandage or applying force via a roller) in order to easily rupture the microspheres thus releasing the microsphere's contents and ensuring a homogeneous hardening/curing reaction throughout the bandage. In the alternative, it is preferable to further include chemical agents capable of rupturing the microspheres in order to release the contents encapsulated within the microspheres. In certain aspects, it may be preferable to include chemical agents capable of rupturing the microspheres and applying shearing forces via manual manipulation to ensure release of the microsphere's contents and to further expedite reactivity of the reactive system.

Exemplary Embodiments

Referring now specifically to the drawings, a medical bandage product in the form of cast tape according to an embodiment of the invention is illustrated in FIG. 1 and shown generally at reference numeral 10. The medical bandage product 10 includes a storage package, such as a pouch 11, in which is contained a roll of flexible cast bandage 12. The bandage 12, coated or impregnated with a curable resin, remains in a flexible condition until the pouch is opened for use. In contrast with prior moisture-curable bandages, the pouch 11 need not be moisture-proof, but can be an inexpensive plastic or coated paper package with sufficient thickness to withstand packaging, shipment and storage until use.

However, in certain aspects, it may be advantageous to store the disclosed medical bandages within moisture-proof packaging to further ensure shelf-life of the medical bandage. For example, in certain aspects, the disclosed medical bandaging product may be provided within a sleeve formed of moisture-impervious material and sealable to prevent entry of moisture. The medical material is preferably positioned in the sleeve and sealed therein against entry of moisture until use. The medical bandage preferably remains stable and unreacted when maintained in substantially moisture-free conditions. In certain embodiments, the moisture-proof packaging is resealable.

Figure 2:
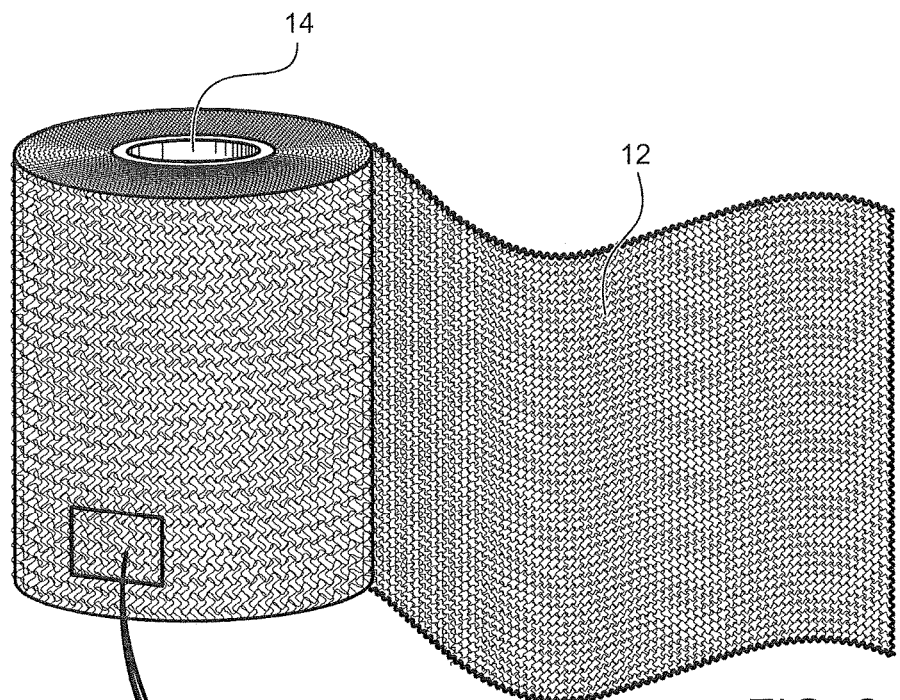
FIG. 2 is a perspective view of the medical cast bandage according to an embodiment of the invention.

Referring now to FIG. 2, the bandage 12 is constructed using a known manufacturing technique, and may be woven, knitted or nonwoven. Bandage 12 may be constructed using any suitable organic or inorganic fibers. Examples of suitable fibers include glass, polyester, polypropylene and blends thereof.

The bandage 12 has a thickness suitable for use as a medical bandage. An example of a suitable thickness would be at least about 1 mm, and preferably between about 2 to about 8 mm. The bandage 12 may be designed so that it has a preferential stretch, strength, and other characteristics in one direction or, in the alternative, may be designed with the fibers laid randomly so that the bandage 12 exhibits uniform properties in all directions. It may also be designed with soft longitudinally extending side edges to aid in the comfort of a patient. The bandage 12 has a weight per unit area of at least about 5 grams per square meter. It can be used alone or it can be reinforced with organic or inorganic fillers, stitches, scrims, laminates, plastic films, or any other suitable reinforcement to obtain the desired splinting properties.

Figure 3:
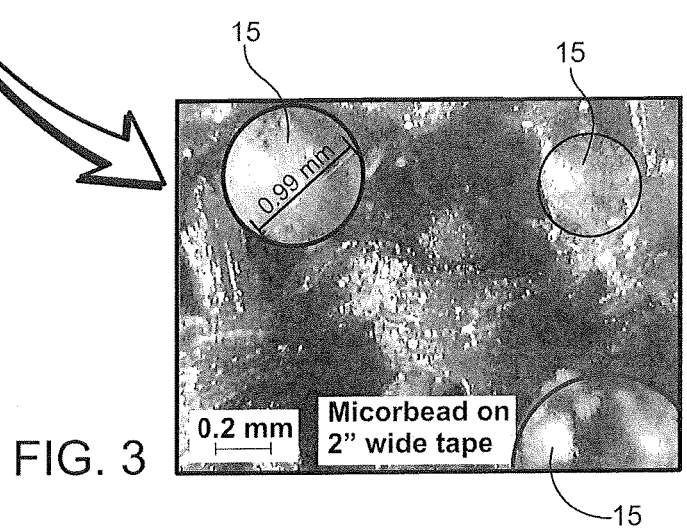
FIG. 3 is an enlarged view of the surface of the medical bandage of FIG. 2, showing microspheres contained in the structure of the medical bandage.

Referring now to FIGS. 2 and 3, the bandage 12 is coated or impregnated with, for example, a curable urethane resin that can be activated to form a rigid cast. Small hollow microspheres 15 are coated onto or incorporated into the structure of the bandage 12. In one preferred embodiment, the microspheres 15 are a polymer type and have a diameter of from 0.2 to 1.5 mm.

In one embodiment of the invention, one subset of the microspheres 15 contains water, and a second subset of the microspheres 15 contains a catalyst that accelerates the hardening reaction. In another embodiment of the invention, each microsphere 15 contains both water and catalyst in an appropriate ratio to achieve the required hardening. In these embodiments the bandage is chemically latent and does not age at the same rate as when the catalyst is present with the urethane. In certain aspects, the number of microspheres is dependent on the size of microspheres and quantity of catalyst and/or water contained in the microspheres.

The disclosed bandage avoids the need to dunk or spray water onto the bandage, thereby avoiding overuse of water that when held against the skin can result in skin masceration.

Two typical formulations of the reaction system is set forth in the following tables:

TABLE 1

| Isonate ↓ 143L or Mondur ↓ CD or polyisocyanate | 50.0% |
| Rubinate ↓XI168 Pluracol ↓P1010 polyol | 46.6% |
| DC-200 Silicone defoaming agent | 0.30% |
| Benzoyl Chloride stabilizer | 0.10% |
| Thancat. DM-70 catalyst | 3.0% |
| | 100% |

TABLE 2

| Isonate 143L or Mondur CD or Polysiocyanate | 50.0% |
| Carbowax PEG 600, Carbowax PEG 4600 | 22.0% |
| Carbowax PEG 8000 Voranol 230-238 Voranol 220-110 | 18.0% |
| Irganox 1010 | 2.0% |
| Antifoam 1400 | 4.0% |
| Methane Sulphonic Acid | 1.0% |
| DMDEE | 3.0% |
| | 100% |

As is shown in FIG. 2, the bandage 12 is rolled onto a core 14 for packaging. The core 14 prevents creasing of the bandage 12 and facilitates rapid, controlled, unrolling of the bandage during application.

Figure 4:
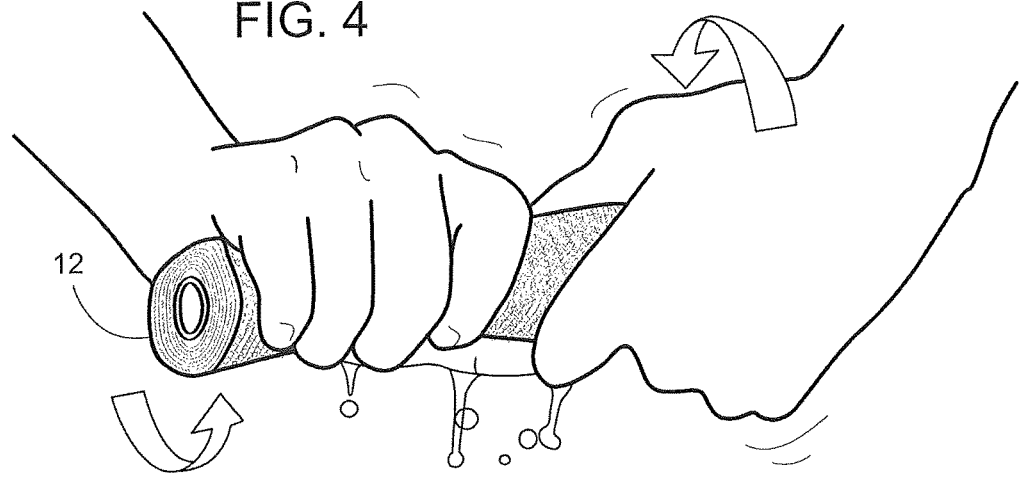
FIGS. 4-7 are sequential views of the steps by which the cast bandage is prepared and applied to a lower leg.
Figure 5:
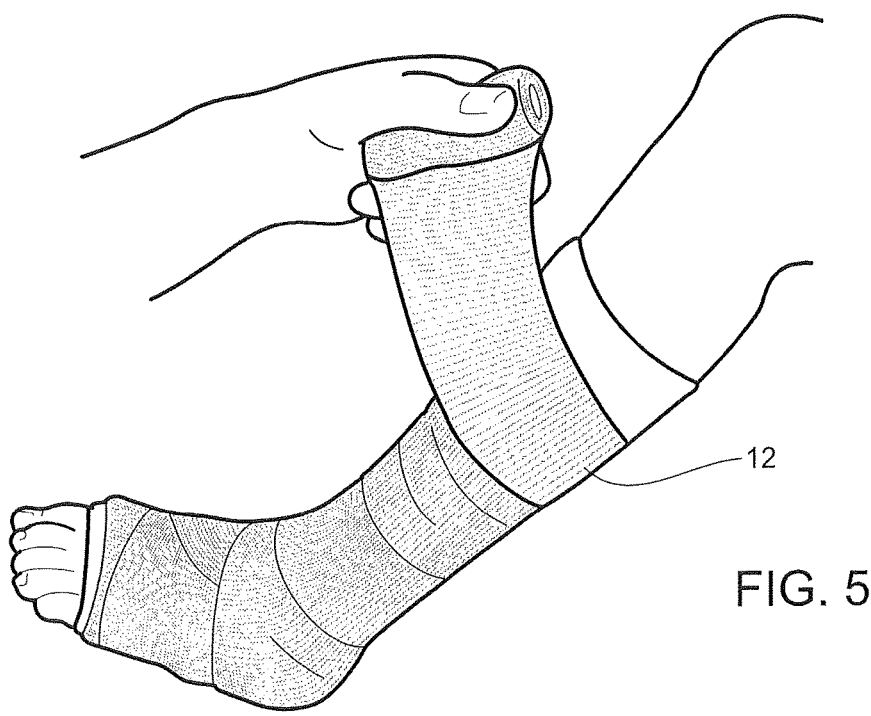
Figure 6:
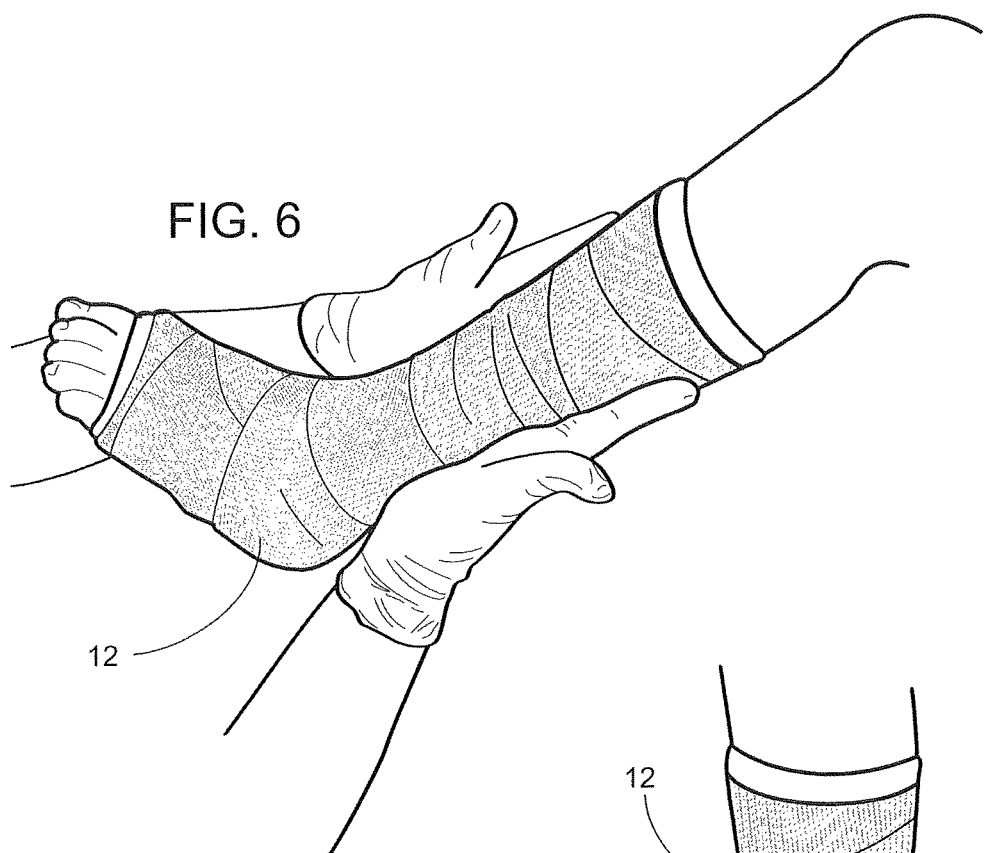

Referring now to FIGS. 4-7, the bandage 12 is applied by removing it from the storage package 11, FIG. 1. As is shown in FIG. 4, the bandage is wrung in the hands. This wringing motion creates enough shear force to shear open or rupture the microspheres 15 thus releasing the catalyst and water. Alternatively, the bandage can be first unrolled from the core 14 and rolled with a hard-surface roller to apply enough force to shear open the microspheres 15. Other methods of shearing microspheres 15 may be used (or alternatively chemical reagents that degrade the microspheres may be used to release, for example, water and/or the catalyst from the microsphere), the only requirement being that the catalyst and water are released from the microspheres 15 so that a chemical reaction of the reactive system is initiated and subsequent hardening (e.g., via a polymerization reaction and/or a moisture curing reaction) of the bandage 12 begins. The bandage is then immediately applied to the limb accordingly, FIG. 5. The applied bandage 12 is smoothed and more closely conformed to the limb while still flexible. Upon hardening, the bandage 12 is sufficiently rigid to maintain the limb in an essentially immobile position, but with enough residual softness to permit slight movement of the limb.

Figure 7:
Figure 8:
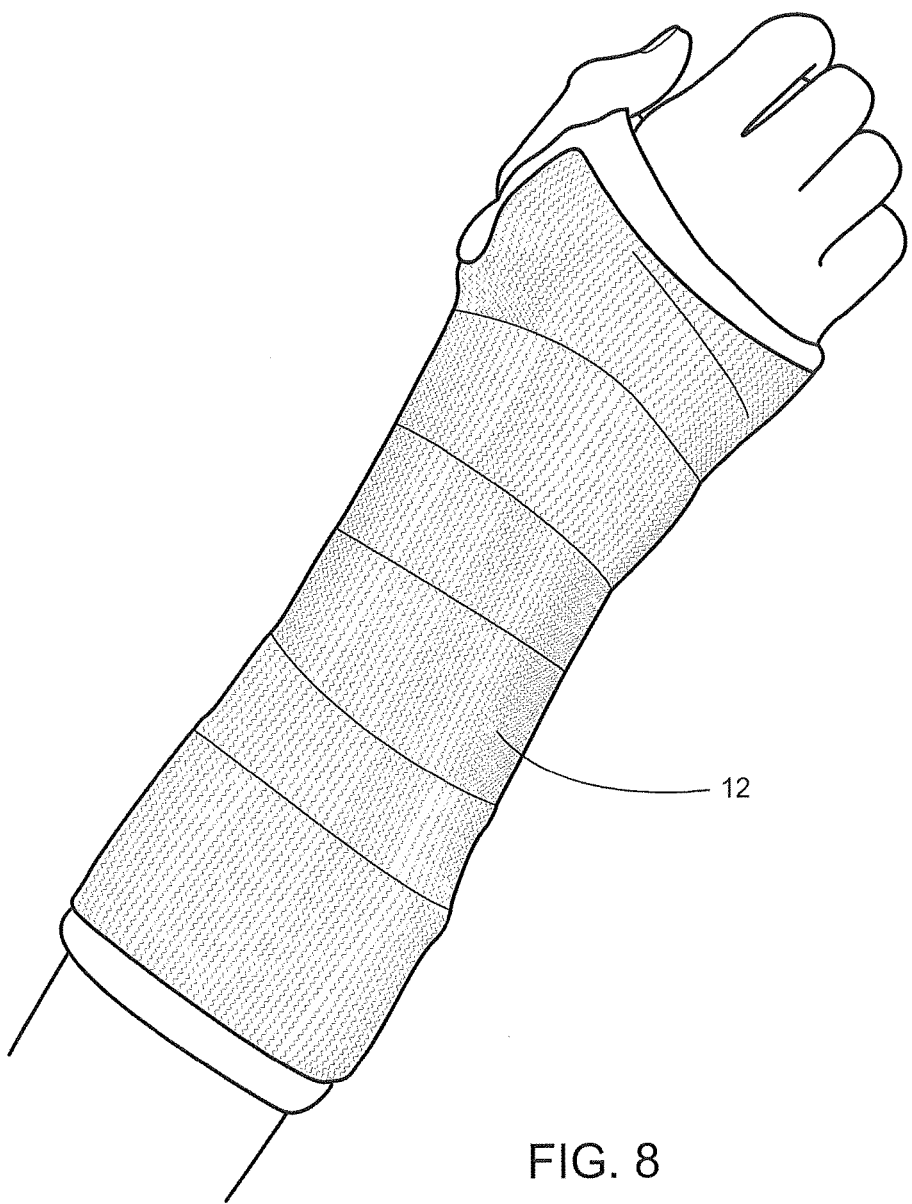
FIG. 8 is a view of the cast bandage as applied to a forearm.

As shown in FIGS. 7 and 8, the bandage 12 can be applied to various limbs. For example, the bandage 12 can be applied to a leg, FIG. 7, or to a forearm, FIG. 8.

Splint

Figure 9:
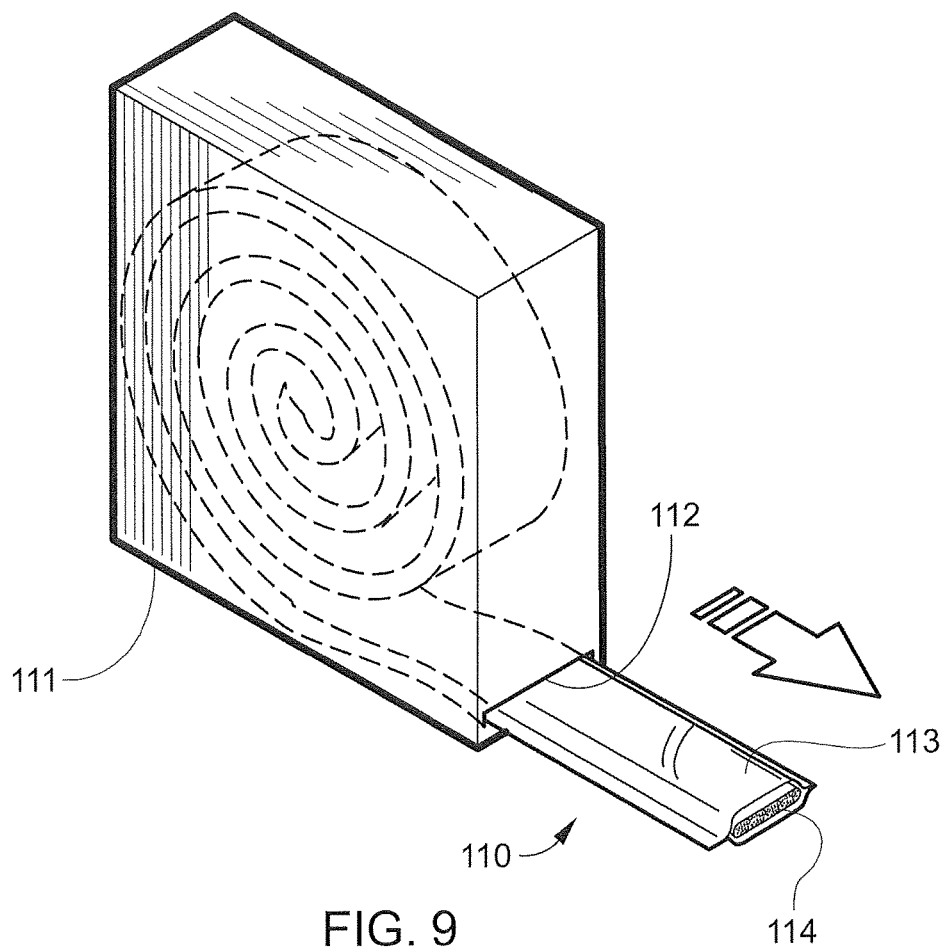
FIG. 9 is a perspective view showing a splint product according to another embodiment of the invention being dispensed from a dispenser.

A medical bandage product 110 for splinting is illustrated in FIG. 9. Bandage product 110 may be sold in any convenient length, such as 30 feet, and is rolled into a coil and positioned in a suitable dispenser 111. Dispenser carton 111 is provided with a slot 112 at one lower corner through which bandage product 110 is dispensed.

The bandage product 110 is formed of an outer elongate sleeve 113, which need not be moisture proof. Sleeve 113 is sealed along opposite, parallel extending sides to form an elongate tube. An elongate medical bandage 114, described in detail below, is positioned within sleeve 113. The bandage 114 is dispensed by pulling the needed amount of material, along with the sleeve 113 in which it is enclosed, out of the carton 111 and severing it with, for example, scissors. The remaining, raw end of the bandage 114 is tucked back into the remaining sleeve 113.

Figure 10:
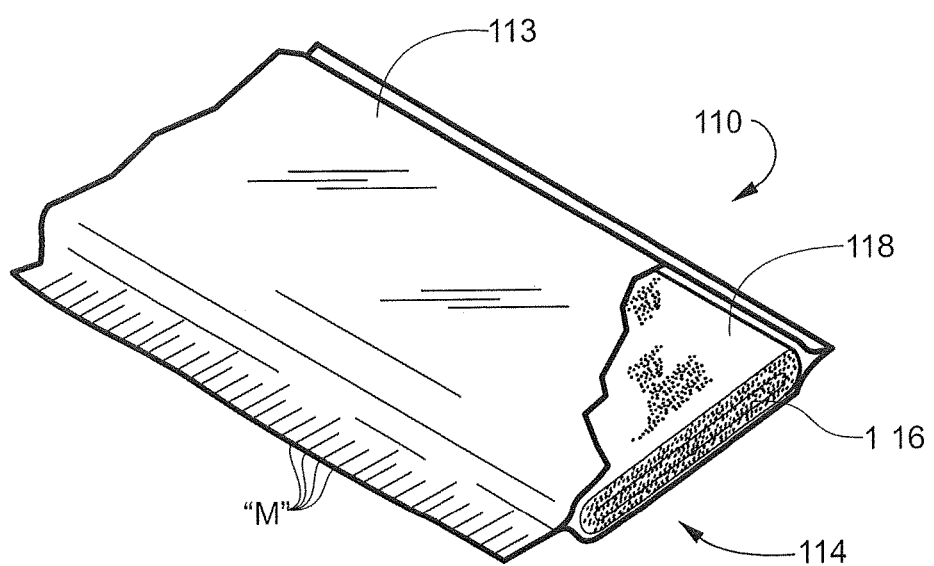
FIG. 10 is a perspective view with parts broken away of a cut length of the splint product.

Referring now to FIG. 10, since the appropriate length of bandage 114 is best determined by measurement, measurement marks "M" may be printed on one edge of the sleeve 113.

Figure 11:
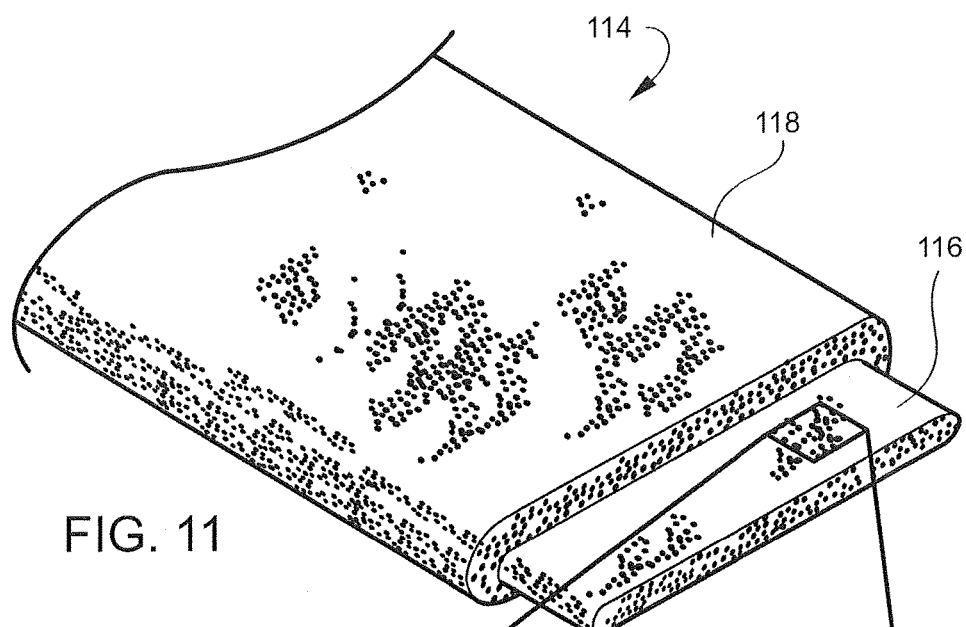
FIG. 11 is a perspective view of a length of the splint material with the substrate layer exposed for clarity.

As shown in FIG. 11, the bandage 114 comprises a substrate 116, which may be woven, knitted or nonwoven. Substrate 116 preferably has a weight per unit area of at least about 50 grams per square meter, and preferably between about 200 to about 700 grams per square meter. The substrate 116 is contained within a tubular wrapping 118 that may be formed of a soft, flexible nonwoven fiber such as polypropylene. This provides a cushioning protective layer between the skin of the patient and substrate 116. The wrapping 118 may also be selected from a wide range of other materials such as open cell or reticulated foam, closed cell foam, soft flexible films and nonwoven materials. Alternatively, the substrate 116 may be packed in the sleeve 113 and enclosed within a protective cushioning layer just before application. This may be accomplished by folding a length of cushioning material around the substrate 116 and securing it in place with, for example, tape or another form of adhesive.

Figure 12:
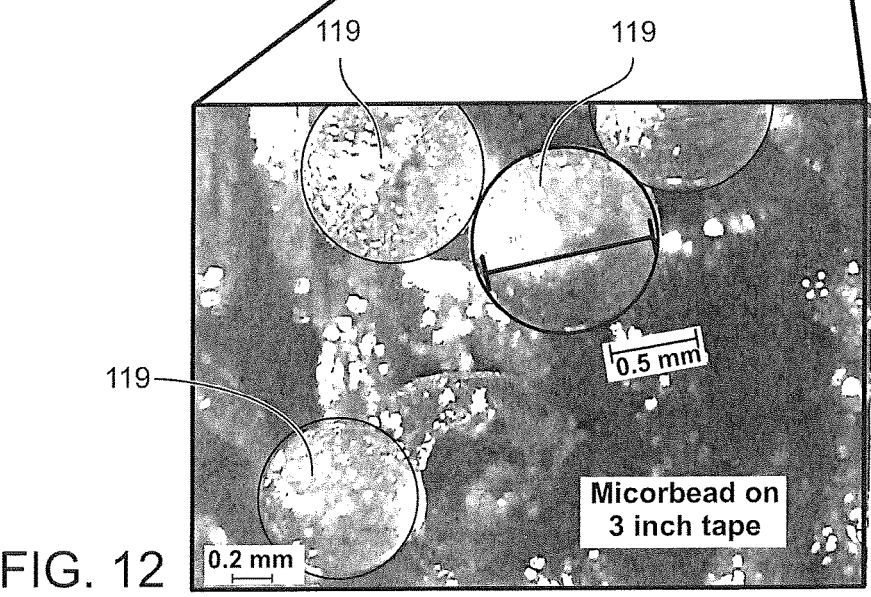
FIG. 12 is an enlarged view of the surface of the medical bandage of FIG. 11, showing microspheres contained in the structure of the medical bandage.

Referring now to FIGS. 11 and 12, the bandage 114 is coated or impregnated with a curable urethane resin that can be activated to form a rigid cast. Small hollow microspheres 119 are then coated onto or incorporated into the structure of the bandage 114. In one preferred embodiment, the microspheres 119 are a polymer type and have a diameter of 0.2 to 1.5 mm.

In one embodiment of the invention, one subset of the microspheres 119 contains water, and a second subset of the microspheres 119 contains a catalyst that accelerates the hardening reaction. In another embodiment of the invention, each microsphere 119 contains both water and catalyst in an appropriate ratio to achieve the required hardening. In these embodiments the bandage is chemically latent and does not age at the same rate as when the catalyst is present with the prepolymer (e.g., urethane) and other reactive components.

The number of microspheres 119 is dependent on the size of microspheres 119 and quantity of catalyst and/or water contained in the microspheres 119.

The disclosed bandage potentially avoids the need to dunk or spray water onto the bandage, thereby avoiding overuse of water that when held against the skin can result in skin masceration.

Two typical formulations of the reaction system is set forth in the following tables:

TABLE 3

| | |
|---|---|
| Isonate ↓ 143L or Mondur ↓ CD or polyisocyanate | 50.0% |
| Rubinate ↓XI168 Pluracol ↓P1010 polyol | 46.6% |
| DC-200 Silicone defoaming agent | 0.30% |
| Benzoyl Chloride stabilizer | 0.10% |
| Thancat. DM-70 catalyst | 3.0% |
| | 100% |

TABLE 4

| | |
|---|---|
| Isonate 143L or Mondur CD or Polysiocyanate | 50.0% |
| Carbowax PEG 600, Carbowax PEG 4600 | 22.0% |
| Carbowax PEG 8000 Voranol 230-238 Voranol 220-110 | 18.0% |
| Irganox 1010 | 2.0% |
| Antifoam 1400 | 4.0% |
| Methane Sulphonic Acid | 1.0% |
| DMDEE | 3.0% |
| | 100% |

Figure 13:
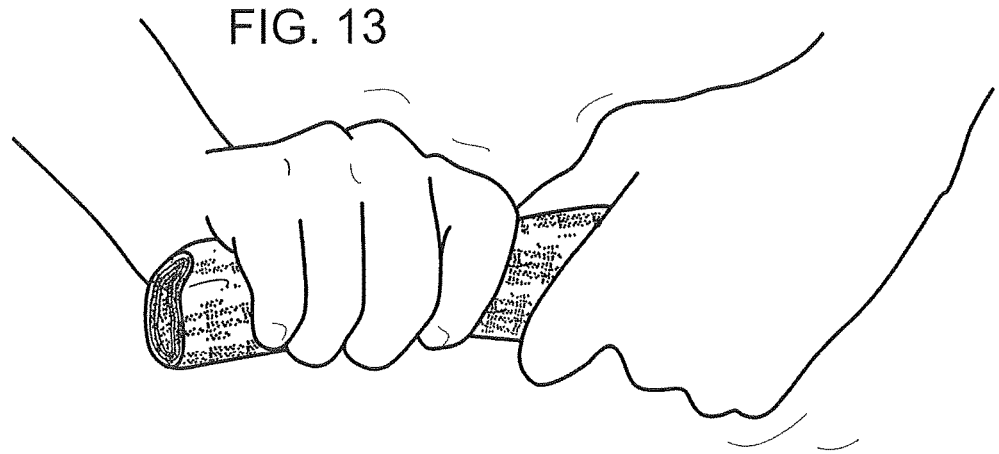
FIG. 13 shows wringing the bandage to rupture the microspheres before application.
Figure 14:
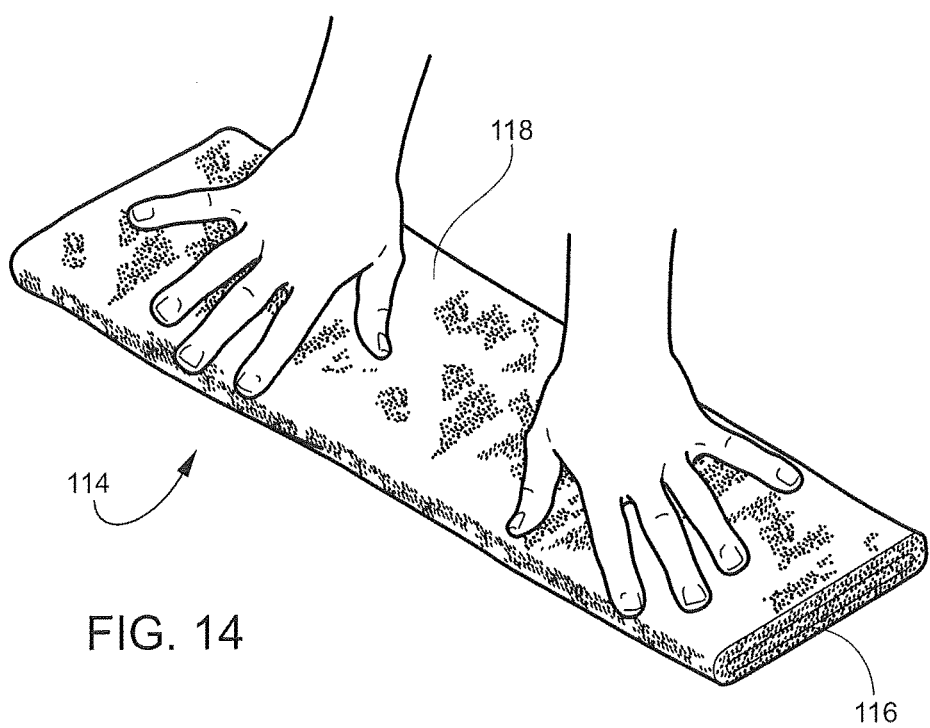
FIG. 14 shows smoothing and straightening of the splint material before application.

As is shown in FIGS. 13-14, the bandage 114 is activated by wringing and massaging the bandage. This wringing and massaging creates enough shear force to open or rupture the microspheres 119 thus releasing the catalyst and water onto the substrate 116 such that a chemical reaction of the reactive system is initiated and subsequent hardening (e.g., via a polymerization reaction and/or moisture curing reaction) begins. Alternatively, the bandage 114 can be rolled with a hard-surface roller to create enough shear force to open or rupture the microspheres 119 thus releasing the catalyst and/or water onto the substrate. Other methods of shearing the microspheres 119 may be used (or alternatively chemical reagents that degrade the microspheres may be used to release, for example, water and/or the catalyst from the microspheres), the only requirement being that the catalyst and water are released from the microspheres 119 so that a chemical reaction of the reactive system is initiated and subsequent hardening (e.g., via a polymerization reaction and/or moisture curing reaction) of the bandage 114 begins. The bandage 114 is smoothed before application, FIG. 14.

Figure 15:
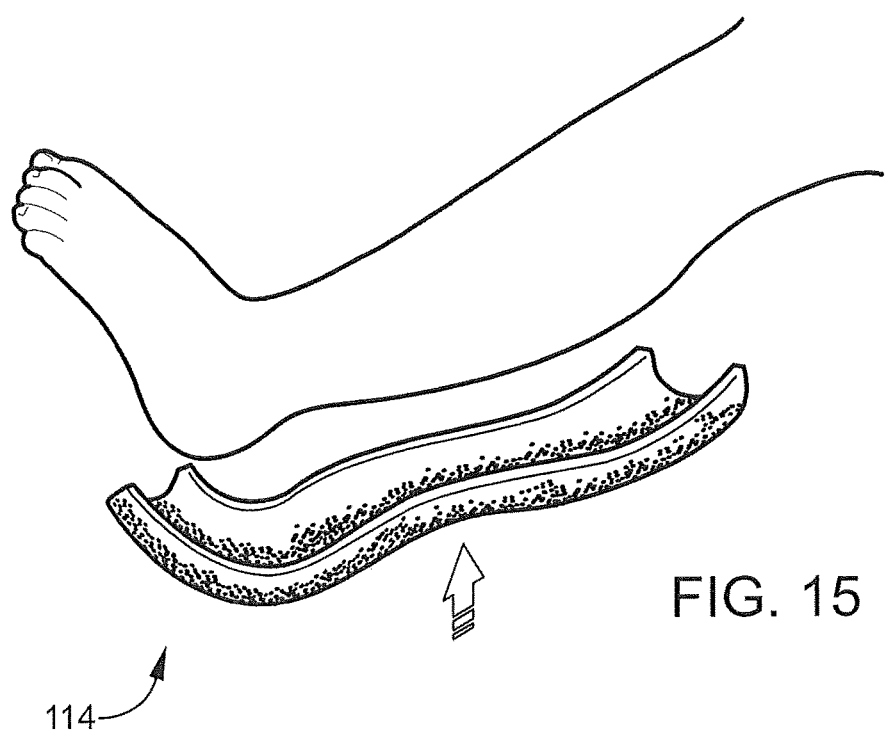
FIGS. 15 and 16 are perspective views of the splint material being placed on an injured limb and being secured into place by a covering wrap.
Figure 16:
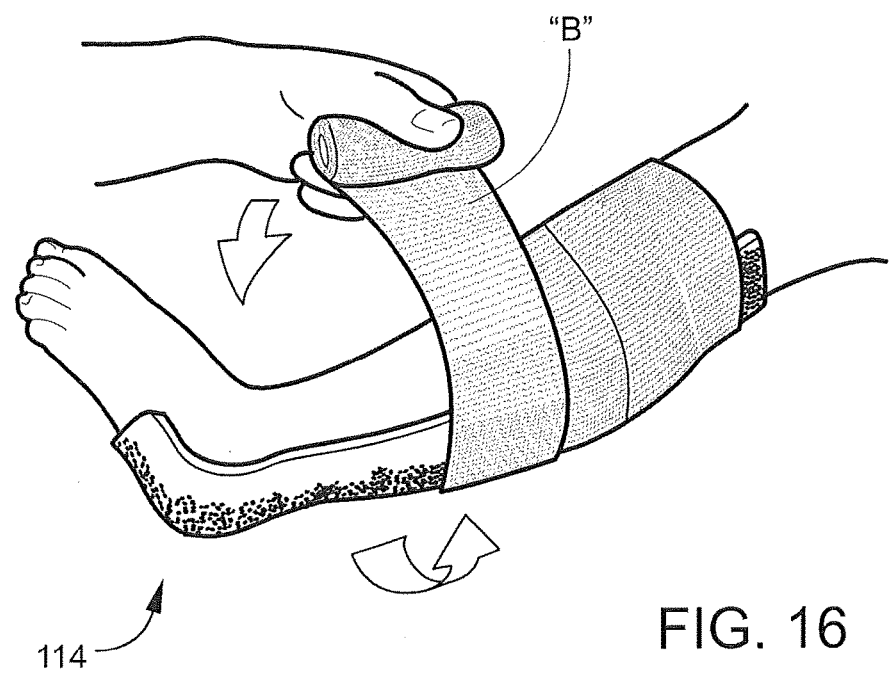

Referring now to FIG. 15, an appropriate length of bandage 114 is formed to the shape of the body member to be immobilized. This particular type of splint, known as a posterior short leg splint, is formed by molding a length of the bandage 114 to the calf and up over the heel and onto the foot. Then, bandage 114 is overwrapped with a known elastic bandage "B", as is shown in FIG. 16.

Figure 17:
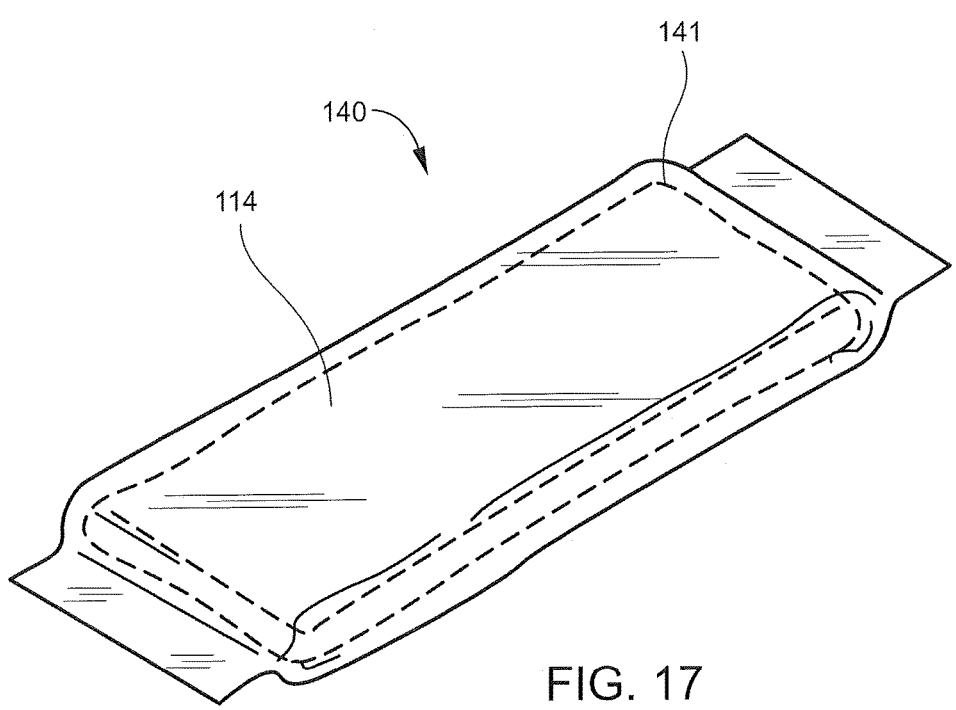
FIG. 17 is a perspective view of a pre-cut splint product stored for use in an envelope until ready for use.

Referring now to FIG. 17, a pre-cut embodiment of a medical bandage product 140 is shown. The medical bandage product 140 comprises an envelope 141 in which is packaged a pre-cut length of the medical bandage 114. The medical bandage 114 is sized according to the desired end use and is labeled as such. The medical bandage 114 may be removed from the envelope 141 and used as is, or cut and shaped as needed to meet the medical requirements of the treating physician and technician.

By way of a further alternative, the resin-coated or impregnated substrate 116 may be packaged in the sleeve 113 without a tubular wrapping. The substrate 116 is removed from the sleeve 113, the microspheres 119 are sheared as described above, and then applied to the patient. To facilitate application of the wrapping, the wrapping may be in the form of a flat sheet of cushion material of sufficient width to extend around the substrate 116 to form a tubular enclosure. The cushion material may be held in its tubular condition around the substrate by, for example, double-sided adhesive tape.

In each of the embodiments disclosed above, the microspheres may be mixed into the resin formulation and applied to the substrates with the resin, being held within the viscous structure of the resin. Alternatively, the microspheres may be distributed (e.g., homogeneously dispersed) through the fabric, embedded in the surface or apertures and openings of the fabric construction. In either case, the surface tension between the resin and the extremely small microspheres is sufficient to maintain the microspheres in contact with the substrate.

In certain aspects, the medical bandage can be packaged as a kit. In this aspect, the kit may include the packaged medical bandage and a roller that aids in applying shear force to the bandage for rupturing the microspheres.

Medical bandage products are described above. Various details of the invention may be changed without departing from its scope. Furthermore, the foregoing description of the preferred embodiments of the invention and the best mode for practicing the invention are provided for the purpose of illustration only and not for the purpose of limitation.

What is claimed is:

1. A medical bandaging product comprising an elongate fabric that is a knitted fabric having monofilament or multifilament yarns including at least one of fiberglass, polyolefin, aramid, and polyamide and that is homogenously impregnated or coated with a reactive system including a plurality of microspheres, wherein:
    each filament of the monofilament or multifilament yarns has a diameter from 0.3 mm to 2 mm;
    the reactive system remains stable in the absence of an activating agent and hardens upon exposure to the activating agent;
    the activating agent is encapsulated in the plurality of microspheres;
    the plurality of microspheres are configured to rupture to release the activating agent; and
    the plurality of microspheres comprise micelles or polymeric microspheres having a diameter ranging from 200 μm to 2000 μm and encapsulate water, a catalyst, or a combination thereof.

2. The medical bandaging product of claim 1, wherein the elongate fabric is surrounded by at least one of a non-woven material, an open cell foam material, or a reticulated foam material.

3. The medical bandaging product of claim 1, wherein the reactive system comprises a polyurethane moisture curing system.

4. The medical bandaging product of claim 3, wherein the reactive system comprises a prepolymer, a polyol, or a combination thereof not encapsulated within the plurality of microspheres.

5. The medical bandaging product of claim 4, wherein the prepolymer is an organic isocyanate selected from the group consisting of methylene diphenyl diisocyanate, toluene diisocyanate, hexamethylene diisocyanate, and isophorone diisocyanate.

6. The medical bandaging product of claim 1, wherein the plurality of microspheres encapsulate an organic isocyanate selected from the group consisting of methylene diphenyl diisocyanate, toluene diisocyanate, hexamethylene diisocyanate, and isophorone diisocyanate.

7. The medical bandaging product of claim 1, wherein the plurality of microspheres are polymeric microspheres comprising at least one of a polyoxyethylene, polypropylene oxide, polylactic acid, polyethylene, polystyrene, poly(methyl methacrylate), polyvinyl pyrrolidone, and polycaprolactone.

8. The medical bandaging product of claim 1, wherein the plurality of microspheres are homogeneous in composition.

9. The medical bandaging product of claim 1, wherein the plurality of microspheres are heterogeneous in composition.

10. The medical bandaging product of claim 1, further comprising an antimicrobial agent coated on the elongate fabric.

11. The medical bandaging product of claim 10, wherein the antimicrobial agent is in the range from 1 $g/m^2$ to 10 $g/m^2$.

12. A method of activating a medical bandaging product comprising an elongate fabric having monofilament or multifilament yarns including at least one of fiberglass, polyolefin, aramid, and polyamide and that is homogenously impregnated or coated with a reactive system including a plurality of microspheres, wherein: each filament of the monofilament or multifilament yarns has a diameter from 0.3 mm to 2 mm; the reactive system remains stable in the absence of an activating agent and hardens upon exposure to the activating agent; the activating agent is encapsulated in the plurality of microspheres; the microspheres are configured to rupture to release the activating agent; and the plurality of microspheres comprise micelles or polymeric microspheres having a diameter ranging from 200 μm to 2000 μm and encapsulate water, a catalyst, or a combination thereof, the method comprising
    physically manipulating the elongate fabric to rupture the plurality of microspheres to homogeneously release the activating agent throughout the medical bandaging product.

13. The method of claim 12, wherein the reactive system comprises a prepolymer, a polyol, or a combination thereof not encapsulated within the plurality of microspheres.

14. The method of claim 13, wherein the prepolymer is an organic isocyanate selected from the group consisting of methylene diphenyl diisocyanate, toluene diisocyanate, hexamethylene diisocyanate, and isophorone diisocyanate.

15. The method of claim 12, wherein the plurality of microspheres are polymeric microspheres comprising at least one of a polyoxyethylene, polypropylene oxide, polylactic acid, polyethylene, polystyrene, poly(methyl methacrylate), polyvinyl pyrrolidone, and polycaprolactone.

* * * * *